(12) United States Patent
Goel

(10) Patent No.: US 9,364,465 B2
(45) Date of Patent: Jun. 14, 2016

(54) THIAZOLIDINEDIONES OF OMEGA-3 POLYUNSATURATED ACIDS AS NEW INSULIN SENSITIZERS FOR TREATING TYPE2 DIABETES

(71) Applicant: Jiva Pharma, Inc., Ann Arbor, MI (US)

(72) Inventor: Om P Goel, Ann Arbor, MI (US)

(73) Assignee: Jiva Pharma, Inc, Ann Arbor, MI (US)

( * ) Notice: Subject to any disclaimer, the term of this patent is extended or adjusted under 35 U.S.C. 154(b) by 0 days.

(21) Appl. No.: 14/780,543

(22) PCT Filed: Mar. 28, 2014

(86) PCT No.: PCT/US2014/032172
§ 371 (c)(1),
(2) Date: Sep. 27, 2015

(87) PCT Pub. No.: WO2014/160936
PCT Pub. Date: Oct. 2, 2014

(65) Prior Publication Data
US 2016/0051521 A1    Feb. 25, 2016

Related U.S. Application Data

(60) Provisional application No. 61/806,311, filed on Mar. 28, 2013.

(51) Int. Cl.
C07D 277/34    (2006.01)
A61K 31/426    (2006.01)
A61K 31/155    (2006.01)

(52) U.S. Cl.
CPC ............. A61K 31/426 (2013.01); A61K 31/155 (2013.01); C07D 277/34 (2013.01)

(58) Field of Classification Search
None
See application file for complete search history.

(56) References Cited

U.S. PATENT DOCUMENTS

2001/0049380 A1    12/2001    Smith
2008/0153889 A1    6/2008    Imig et al.
2011/0281921 A1    11/2011    Srebnik et al.

*Primary Examiner* — Laura L. Stockton
(74) *Attorney, Agent, or Firm* — Technology Law PLLC; Karen L Kimble

(57) ABSTRACT

The present invention relates to thiazolidinedione derivatives of omega-3 fatty acids as insulin sensitizers, and their use in treating Type2 diabetes, obesity, hypertriglyceridemia, cardiovascular diseases, metabolic diseases, inflammation, renal anemia, and/or Alzheimer's disease: and for modulating activity of peroxisome proliferator-activated receptors (PPARs).

16 Claims, 1 Drawing Sheet

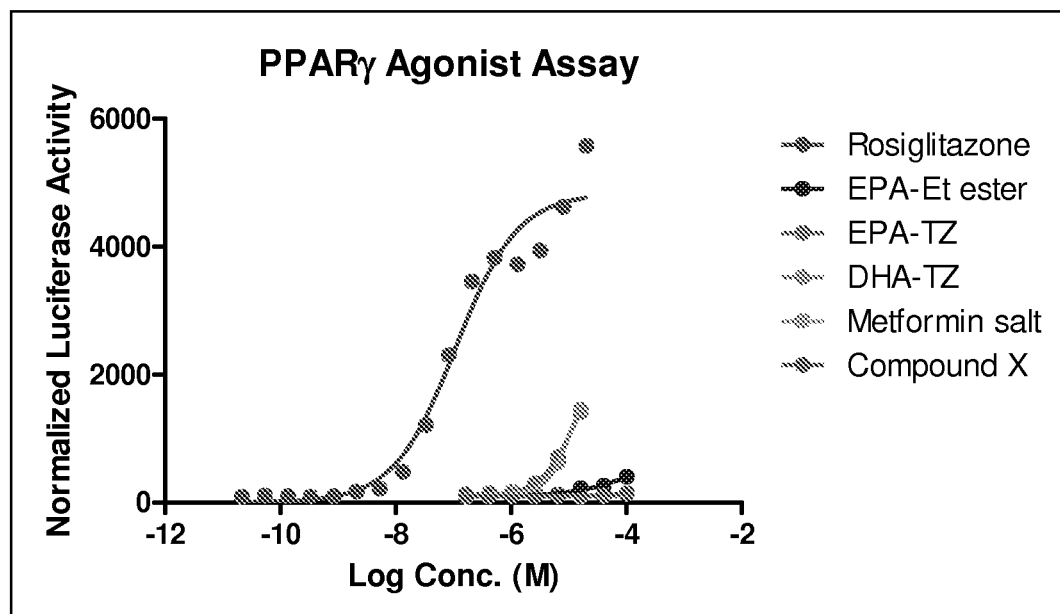

THIAZOLIDINEDIONES OF OMEGA-3 POLYUNSATURATED ACIDS AS NEW INSULIN SENSITIZERS FOR TREATING TYPE2 DIABETES

FIELD OF THE INVENTION

The present invention relates to novel thiazolidinedione derivatives of omega-3 fatty acids used as insulin sensitizers for treating Type2 diabetes, obesity, hypertriglyceridemia, cardiovascular diseases, metabolic diseases, inflammation, cancer, renal anemia, Alzheimer's disease; and for modulating activity of peroxisome proliferator-activated receptors (PPARS).

BACKGROUND OF THE INVENTION

Once diagnosed, Type2 diabetes (T2D) is a life-long disease of elevated plasma glucose levels caused by the inability of the pancreas to produce sufficient insulin and/or muscle, fat, and liver cells to utilize available insulin for the uptake of glucose, known as insulin resistance. Insulin resistance simply means below normal glucose lowering effect of insulin. Worldwide, the incidence of T2D is rising rapidly with increasing obesity from diets of high-carbohydrates and high-fats and little exercise. According to the American Diabetes Association, in early 2011, 25.8 million children and adults in the United States had diabetes. American Academy of Pediatricians has issued its first-ever guidelines for T2D, a grim milestone for a disease that was rare in children before obesity rates began to rise (*Wall Street Journal*, Jan. 28, 2013; A3). Fasting glucose levels and glycosylated hemoglobin (HbA1C) are used as estimating markers for undiagnosed diabetes, and pre-diabetic conditions.

Cardiovascular disease from dyslipidemia and T2D are closely associated. Insulin resistance is caused by the accumulation of lipids in the liver and other tissues. It is not yet known whether fatty liver causes insulin resistance or insulin resistance leads to storage of fat in the liver. An insulin sensitizer improves insulin's ability to stimulate cellular glucose uptake, leading to reduced levels of plasma glucose (P. A. Carpino, et al., "Beyond PPARs and Metformin: New Insulin Sensitizers for the Treatment of Type 2 Diabetes", *Annual Reports in Medicinal Chem.*, 47, 177-192 (2012)). Thus, it appears possible that by decreasing insulin resistance, and concomitantly, also lowering levels of circulating low density lipid particles, the dual benefits of treating T2D, and improved cardiovascular health may be realized.

Omega-3 oils or omega-3 fatty acids are naturally occurring, straight-chain (16-24 carbons) fatty carboxylic acids (PUFAs), essential for normal metabolism in humans and other animals. Since the omega-3 fatty acids are not synthesized by the human body, they are recommended to be taken as dietary supplements in 1-4 grams daily for cardiovascular health benefits, preventing strokes, and reducing blood pressure. (J. Delgado-Lista et al., "Long Chain Omega-3 Fatty Acids and Cardiovascular Disease: A Systematic Review", *The British J. of Nutrition* 107 Suppl. 2, S201-13 (June 2012)).

Omega-3 fatty acids have 3-6 conjugated carbon-carbon double bonds, and are so named as the first carbon with unsaturation is $3^{rd}$ carbon from the distal carboxylic acid carbon. All double bonds are in the cis configuration. Among the omega-3 fatty acids eicosapentanenoic acid (EPA, 20 carbons, 5 conjugated carbon-carbon double bonds), docohexaenoic acid (DHA, 22 carbons, 6 conjugated double bonds) and α-linolenic acid (ALA, 18 carbons, 3 conjugated double bonds) are the most studied pharmacologically. Pharmaceutically effective mixtures of ethyl esters of eicosapentaenoic acid and docosahexaneoic acid are prescribed to treat hypertriglyceridemia. For example, the drug Lovaza™ (developed by Reliant Pharmaceuticals and marketed by GlaxoSmithKline (GSK)) is approved by the U.S. FDA to lower very high triglyceride levels ≥2500 mg/dl. In July 2012, the U.S. FDA approved Amarin's Vascepa™ (icosapent ethyl, EPA ethyl ester) for treating severe hypertriglyceridemia (U.S. Pat. No. 8,188,146).

The mechanisms by which omega-3 fatty acids lower circulating triglycerides are being actively studied. One theory is that the omega-3 fatty acids inhibit the formation of VLDL particles in the liver, which in turn lowers the level of circulating triglycerides. Eicosopentaneoic acid (20:5) (EPA) increases fatty acid and glucose uptake and glucose oxidation in cultured human skeletal muscle cells (V. Aas, et al., *J. of Lipid Res.*, 47, 366-374 (2006)). It is possible that they act through similar cellular pathways of lipid and lipoprotein metabolism, such as induction of the beta-oxidation pathway, like fibric acids, such as benzfibrate, fenofibrate and gemfibrozil. However, unlike the fibrates, which are peroxisome proliferator-activator receptor alpha (PPARα) agonists, the omega-3 acids DHA and EPA are peroxisome proliferator-activator receptor gamma (PPARγ) activators. Both receptors have a distinct tissue expression; PPARα is expressed at high levels in the liver, whereas PPARγ is expressed in many tissues, with the highest concentrations in adipose and skeletal muscle cells (A. Banga, et al., "Adiponectin Translation is Increased by the PPARgamma Agonists Pioglitazone and Omega-3 Fatty Acids", *Am. J. Physiol. Endocrinol. Metab.* 296(3), 13-14 (March 2009)). This distinction is very significant, as discussed later in this specification.

The thiazolidinediones (TZDs), such as troglitazone, (RS)-5-(4-[(6-hydroxy-2,5,7,8-tetramethylchroman-2-yl)methoxy]benzyl)thiazolidine-2,4-dione (Rezulin®), trademark of Warner-Lambert Company), rosiglitazone, (RS)-5-[4-(2-[methyl(pyridine-2-yl)amino]ethoxy)benzyl]thiazolidine-2,4-dione (Avandia®), trademark of SmithKline Beecham) and pioglitazone, (RS)-5-(4-[2-(5-ethylpyridin-2-yl)ethoxy]benzyl)thiazolidine-2,4-dione (Actos®, trademark of Takeda Pharmaceutical Company) are highly effective insulin sensitizers that were approved by the FDA and market launched in the 1990s for treating T2D. The TZDs, as a class, are peroxisome proliferator-activated receptor gamma (PPARγ) agonists. However, the safety profiles of the above glitazones, after wide-spread use, led to an early withdrawal of troglitazone (due to idiosyncratic hepatitis); and after more than a decade of rosiglitazone use, it was withdrawn (due to concerns of coronary heart disease). In November 2013, following extensive reviews, the FDA announced removal of certain restrictions on prescribing rosiglitazone and confirmed its use as one of the standards-of-care in treating diabetes patients. Pioglitazone's continues to be prescribed with monitoring of its potential side-effects on cardiac health and bladder cancer (Wikipedia).

The thiazolidinone moiety is the common structural pharmacophore in all of the above glitazones, responsible for the PPARγ agonist activity. It is connected at its only saturated carbon center via a methylene bridge to a p-phenoxyethylene group, which is further modified with unique heterocyclic ring structures for each of the above three glitazones.

Omega-3 (or n-3) polyunsaturated fatty acids (PUFAs) and their metabolites are natural ligands for peroxisome proliferator receptor activator gamma (PPARγ) and, due to the effects of PPARγ on cell proliferation, survival, and differentiation, are potential anticancer agents. (I. J. Edwards, et al., "Omega-3 Fatty Acids and PPARgamma in Cancer", *PPAR Res.*, 358052 (2008)).

BRIEF SUMMARY OF THE INVENTION

Omega-3 acids offer an unexplored and unusual structural motif of long aliphatic carbon straight-chains rich with 4-6 conjugated, all cis double bonds of 8-12 n electrons in contrast to an aromatic phenoxy ring (8 π electrons) as found in the glitazones.

Mono- and poly-unsaturated fatty acids, including the omega-3 acids, have been shown to interact with, and in some cases activate the transcriptional activity of PPARγ (see for example, Xu H E, et al., "Molecular Recognition of Fatty Acids by Peroxisome Proliferator-activated Receptors", *Mol. Cell* [Internet] 3(3), 397-403 (1999 Mar. 17); S. A. Kliewer, et al., "Fatty Acids and Eicosanoids Regulate Gene Expression Through Direct Interactions with Peroxisome Proliferator-activated Receptors Alpha and Gamma", *Proc. Natl. Acad. Sci. USA* [Internet], 94(9), 4318-23 (1997 Apr. 17)). Because the omega-3 acids are already known to be mild PPARγ ligands, and because they have additional non-PPAR-mediated health benefits, the present invention modifies the carboxylic acid of omega-3 acids to increase their PPARγ binding and activation activity. This was accomplished by covalently joining a thiazolidinedione group to the methylene group derived from the carboxylic acid of EPA and DHA omega-3 acids. The resulting compounds have "souped-up" PPARγ activity, and/or other unique biological properties. Surprisingly, these compounds having both PUFA-like moieties and a thiazolidinedione functionality have not been synthesized or reported upon. While not wishing to be bound by theory, it is believed that these thiazolidinedione derivatives would be more lipophilic than the PUFAs, cross the blood brain barrier, which may in turn lead to benefits in treating neurological disorders, including Alzheimer's disease. This theory must be proven by testing as it is unpredictable whether such properties are possible.

These thiazolidinedione PUFA derivatives of the present invention are formed by reduction of the carboxylic acid of the omega-3s to an end methylene moiety becoming a bridge linked to the thiazolidinone ring. The following structure depicts these present compounds of Formula (I):

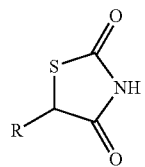

Formula (I)

wherein: R is joined from the methylene moiety formed by reduction of the carboxylic acid of cis,cis,cis-7,10,13-hexadecatrienoic acid (HTA), cis,cis,cis-9,12,15-octadecatrienoic acid (ALA), cis,cis,cis-6,9,12,15-octadecatetraenoic acid (SDA), cis,cis,cis-11,14,17-eicosatrienoic acid (ETE), cis,cis,cis,cis-8,11,14,17-eicosatetraenoic acid (ETA); cis,cis,cis,cis,cis-5,8,11,14,17-eicosapentanenoic acid (EPA), cis,cis,cis,cis,cis-6,9,12,15,18-heneicosapentaenoic acid (HPA), cis,cis,cis,cis,cis-7,10,13,16,19-docosapentaenoic acid (DPA), cis,cis,cis,cis,cis,cis-4,7,10,13,16,19-docosahexaenoic acid (DHA), cis,cis,cis,cis,cis-9,12,15,18,21-tet-racosapentaenoic acid (TPA) or cis,cis,cis,cis,cis,cis-6,9,12,15,18,21-tetracosahexaenoic acid (THA).

The link between T2D and dyslipidemia, and resulting coronary heart disease is unequivocal. Dyslipidemia affects 50% of patients with T2D, is characterized by high triglyceride levels, high LDL and low HDL particles (K. Vijayaraghavan, "Treatment of dyslipidemia in patients with Type2 diabetes", *Lipid Health Dis.* 9, 144 (2010). Eicosopentaneoic acid (20:5) (EPA) increases fatty acid and glucose uptake and glucose oxidation in cultured human skeletal muscle cells (V. Aas, et al., *J. of Lipid Res.*, 47, 366-374 (2006)). Pharmaceutically effective mixtures of ethyl esters of eicosapentaenoic acid (EPA) and docosahexaneoic acid (DHA) are approved by the US FDA to treat hypertriglyceridemia, as is eicosapentaenoic acid ethyl ester, alone.

Additionally, this invention treats T2D with a formulation of omega-3 thiazolidinones of Formula (I) and omega-3 acids. Preferably, the omega-3 acids are eicosapentaenoic acid (EPA), or its ethyl ester, or docosohexaneoic acid (DHA), or its ethyl ester.

BRIEF DESCRIPTION OF THE DRAWINGS

FIG. 1 graphically represents the biological data obtained in the PPARγ agonist assays.

DETAILED DESCRIPTION OF THE INVENTION

It is understood that the terminology used herein is for the purpose of describing particular embodiments only and is not intended to be limiting. As used in this specification, the singular forms "a", "an", and "the" include plural referents unless the content clearly indicates otherwise. The following terms in the Glossary as used in this application are to be defined as stated below and for these terms, the singular includes the plural.

Various headings are present to aid the reader, but are not the exclusive location of all aspects of that referenced subject matter and are not to be construed as limiting the location of such discussion.

Also, certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

GLOSSARY

ALA means α-linolenic acid or cis,cis,cis-9,12,15-octadecatrienoic acid, having 18 carbons, 3 cis double bonds, that is modified by reduction of the carboxylic acid to a methylene moiety to be R of Formula (I), RS-5-((9Z,12Z,15Z)-octadeca-6,9,12-trien-1-yl)thiazolidine-2,4-dione, as shown by the formula below:

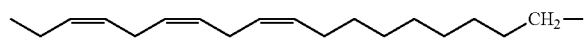

DHA means cis,cis,cis,cis,cis,cis-4,7,10,13,16,19-docosahexaenoic acid or docosahexaenoic acid, having 22 carbons, 6 cis double bonds, that is modified by reduction of the carboxylic acid to a methylene moiety to be R of Formula (I), RS-5-((4Z,7Z,10Z,13Z,16Z,19Z)docosa-4,7,10,13,16,19-hexaen-1-yl)thiazolidine-2,4-dione, as shown by the formula below:

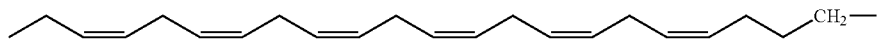

DPA means cis,cis,cis,cis,cis-7,10,13,16,19-docosapentaenoic acid or docosapentaenoic acid, having 22 carbons, 5 cis double bonds, that is modified by reduction of the carboxylic acid to a methylene moiety to be R of Formula (I), RS-5-((7Z,10Z,13Z,16Z,19Z)docosa-7,10,13,16,19-pentaen-1-yl)thiazolidine-2,4-dione, as shown by the formula below:

HTA means cis,cis,cis-7,10,13-hexadecatrienoic acid, having 16 carbons, 3 cis double bonds, that is modified by reduction of the carboxylic acid to a methylene moiety to be R of Formula (I), RS-5-((7Z,10Z,13Z)-hexadeca-7,10,13-trien-1-yl)thiazolidine-2,4-dione, as shown by the formula below:

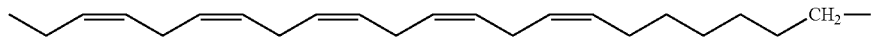

EPA means cis,cis,cis,cis,cis-5,8,11,14,17-eicosapentanenoic acid or eicosapentanenoic acid, having 20 carbons, 5 cis double bonds, that is modified by reduction of the carboxylic acid to a methylene moiety to be R of Formula (I), RS-5-((5Z,8Z,11Z,14Z,17Z)-eicosa-5,8,11,14,17-pentaen-1-yl)thiazolidine-2,4-dione, as shown by the formula below:

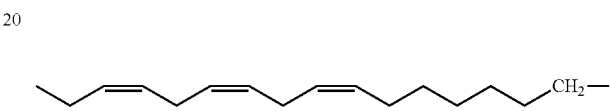

ETA means cis,cis,cis,cis-8,11,14,17-eicosatetranoic acid or eicosatetraenoic acid, having 20 carbons, 4 cis double bonds, that is modified by reduction of the carboxylic acid to a methylene moiety to be R of Formula (I), RS-5-((8Z,11Z,14Z,17Z)-eicosa-8,11,14,17-tetraen-1-yl)thiazolidine-2,4-dione, as shown by the formula below:

SDA means cis,cis,cis,cis-6,9,12,15-octadecatetraenoic acid or stearidonic acid, having 18 carbons, 4 cis double bonds, that is modified by reduction of the carboxylic acid to a methylene moiety to be R of Formula (I), RS-5-((6Z,9Z,12Z,15Z)-octadeca-6,9,12,15-tetraen-1-yl)thiazolidine-2,4-dione, as shown by the formula below:

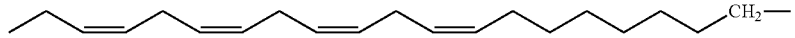

ETE means cis,cis,cis-11,14,17-eicosatrienoic acid or eicosatrienoic acid, having 20 carbons, 3 cis double bonds, that is modified by reduction of the carboxylic acid to a methylene moiety to be R of Formula (I), RS-5-((11Z,14Z,17Z)-eicosa-11,14,17-trien-1-yl)thiazolidine-2,4-dione, as shown by the formula below:

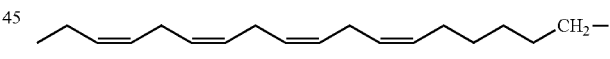

HPA means cis,cis,cis,cis,cis-6,9,12,15,18-heneicosapentaenoic acid or heneicosapentaenoic acid, having 21 carbons, 5 cis double bonds, that is modified by reduction of the carboxylic acid to a methylene moiety to be R of Formula (I), RS-5-((6Z,9Z,12Z,15Z,18Z)-heneicosa-6,9,12,15,18-pentaen-1-yl)thiazolidine-2,4-dione, as shown by the formula below:

THA means cis,cis,cis,cis,cis,cis-6,9,12,15,18,21-tetracosahexaeonic acid, having 24 carbons, 6 cis double bonds, that is modified by reduction of the carboxylic acid to a methylene moiety to be R of Formula (I), RS-5-((6Z,9Z,12Z,15Z,18Z,21Z)-tetracosa-6,9,12,15,18,21-hexaen-1-yl)thiazolidine-2,4-dione, as shown by the formula below:

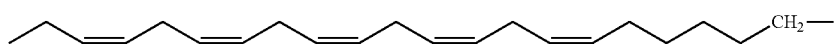

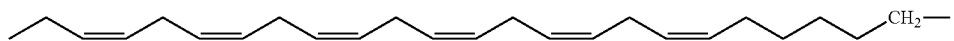

TPA means cis,cis,cis,cis,cis-9,12,15,18,21-tetracosapentaeonic acid, having 24 carbons, 5 cis double bonds, that is modified by reduction of the carboxylic acid to a methylene moiety to be R of Formula (I), RS-5-((9Z,12Z,15Z,18Z,21Z)-tetracosa-9,12,15,18,21-pentaen-1-yl)thiazolidine-2,4-dione, as shown by the formula below:

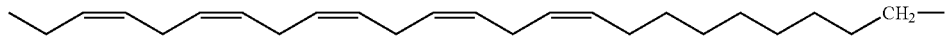

DIBAH means diisobutylalumunim hydride
DMG means dimethylglyoxime
h means hour(s)
min means minute(s)
Omega-3 fatty acids means naturally occurring, straight-chain $C_{16}$-$C_{24}$ fatty carboxylic acids
PUFA means polyunsaturated fatty acids that are either naturally occurring omega-3 fatty acids or derivatives thereof
RT means room temperature, about 22-25° C., or ambient temperature
T2D means Type2 diabetes The present invention provides thiazolinediones derived from the above polyunsaturated omega-3 fatty acids (PUFAs) as insulin sensitizers to treat Type2 diabetes (T2D), and as depicted by the following Formula (I)

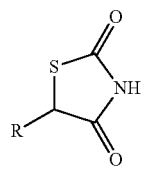

Formula (I)

R is joined from the methylene group formed by reduction of the carboxylic acid of cis,cis,cis-7,10,13-hexadecatrienoic acid (HTA), cis,cis,cis-9,12,15-octadecatrienoic acid (ALA), cis,cis,cis,cis-6,9,12,15-octadecatetraenoic acid (SDA), cis,cis,cis-11,14,17-eicosatrienoic acid (ETE), cis,cis,cis,cis-8,11,14,17-eicosatetraenoic acid (ETA); cis,cis,cis,cis,cis-5,8,11,14,17-eicosapentanenoic acid (EPA), cis,cis,cis,cis,cis-6,9,12,15,18-heneicosapentaenoic acid (HPA), cis,cis,cis,cis,cis-7,10,13,16,19-docosapentaenoic acid (DPA), cis,cis,cis,cis,cis,cis-4,7,10,13,16,19-docosahexaenoic acid (DHA), cis,cis,cis,cis,cis-9,12,15,18,21-tetracosapentaeonic acid (TPA) or cis,cis,cis,cis,cis-6,9,12,15,18,21-tetracosahexaeonic acid (THA).

In 2013 the US FDA approved the Takeda drug Alogliptin (2-({6-[(3R)-3-aminopiperidin-1-yl]-3-methyl-2,4-dioxo-3,4-dihydropyrimidin-1(2H)-yl}methyl)benzonitrile, that is a dipeptidyl peptidase-4 inhibitor (DPP-4) to treat T2D in three formulations: 1) as a stand-alone with the brand-name Nesina®; 2) combined with metformin using the name Kazano®, and 3) when combined with pioglitazone using the name Oseni®. Also Takeda Co., the inventor of pioglitazone, has reintroduced the combination, Oseni®, as a safer alternative to the largely withdrawn pioglitazone alone.

Thus, the present invention compounds of Formula (I) are used to treat T2D in combination with omega-3 acids, especially eicosapentaenoic acid (EPA) or its ethyl ester, or docosohexaneoic acid (DHA) or its ethyl ester; or metformin and/or rosiglitazone or pioglitazone. In a clinical study of combination therapy of fenofibrate, which lowers triglycerides and raises HDL, and rosiglitazone, paradoxically and unexepectedly a substantial fall in HDL levels was observed (Lena Normen, et al., *Diabetes Care,* 27(9), 2241-2242 (September 2004)). However, unlike fenofibrate, which is a peroxisome proliferator-activator receptor alpha (PPARα) agonist, rosiglitazone is a PPARγ activator. Both receptors have a distinct tissue expression. PPARα is expressed at high levels in the liver; whereas PPARγ is expressed in many tissues, with the highest concentrations in adipose and skeletal muscle cells.

Because the omega-3 acids are already known to be mild-PPARγ agonists, the present invention utilizes the formation of compounds by modifying the carboxylic acid of the PUFA and covalently joining a thiazolidinedione functionality and has tested if these compounds have "souped-up" PPARγ activity, and/or other unique biological properties. Such compounds can be used alone as a pharmaceutically-acceptable formulation, such as a tablet or other formulations, or in combination with a thiaglitazone such as rosiglitazone or pioglitazone, in treating T2D, and possibly also assuring safe cardiovascular health and minimizing other known side-effects of the latter drugs. This combination treatment can be administered either as a single formulation or concurrently administered.

Alzheimer' Disease:

The prevalence and incidence of Alzheimer's disease, and its devastating effects on the lives of patients and care giver families are well known. The health care costs to society are onerous, and will continue to grow with the aging population. Enormous strides have been made in understanding the pathology of the disease which leads to the build-up of amyloid plaques in the brain, which are aggregates of amyloid beta (Aβ) peptides. Fundamental advances have been made in discovering inhibitors of the extra-cellular and intra-cellular neuronal biochemical enzymes such as β-secretage (BACE1) or γ-secretase (GS) to stop the amyloid or intraneuronal τ-tangles build-up; and even reverse these processes through treatment with specific monoclonal antibodies. However, in spite of massive scientific research and investments in reversing the cognitive decline of AD, these have yielded scant benefits. Consensus is emerging that the best approach would be to treat before the disease has progressed too far, and even before disease symptoms become apparent. Multi-targeted Alzheimer's drugs, for example dual BACE/acetylcholineesterase inhibition or GSM/PPARγ active agents would offer additional benefits (Harrie J. M. Gisjen, et al., "Secretase Inhibitors and Modulators as a Disease-Modifying Approach Against Alzheimer's Disease", *Annual Reports in Medicinal Chem.,* 47, 55-69 (2012)).

The presence of omega-3 fatty acids, especially DHA in the brain is ubiquitous. Clinical studies in 4 year old children support the beneficial effects of docohexaenoic acid (DHA) on cognitive function (NCT 00351624; 2006-2008; sponsored by Martek BioSciences Corporation). It would be an interesting study to follow such treated children over decades regarding the incidence of onset of symptoms of Alzheimer's disease relative to the untreated group. In the meantime, it is worth exploring in a prospective study, if the DHA thiaglitazone, a PPARγ agonist, either alone, or in combination with a gamma secretase modulator (GSM), or other prescribed clinical agents would slow down the decline of cognitive function in pre-AD patients.

The general synthesis of the compounds of Formula (I) is described in the general scheme below and the procedures are based on the literature provided below.

General Reaction Scheme

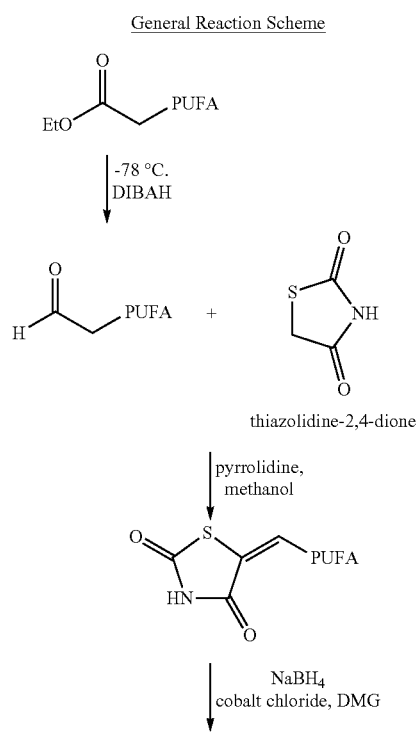

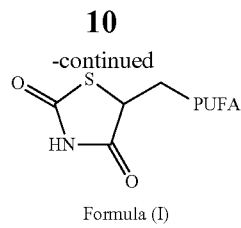

Formula (I)

The procedures used in the examples are based on reported literature on the synthesis of thioazolidinediones, see for example:

1) Les A. Pucko, et al., "Optimization of the Reduction of a 5-Benzylidenethiazolidine-2,4-dione Derivative Supported by the Reaction Resonce Surface Analysis: Synthesis of Pioglitazone Hydrochloride", *Org. Proc. Res. Dev.*, 8, 157-162 (2004);

2) Thomas Mendgen, et al., "Privileged Scaffolds or Promiscuous Binders: A Comparative Study on Rhodanines and Related Heterocycles in Medicinal Chemistry", *J. Med. Chem.*, 55, 743-753 (2011);

3) O. P. Goel, et al., "N-tert-butoxycarbonyl-L-Leucinal", *Org. Syn.* 8, 68-70 (1993); and 4) H. F. Anwar, et al., "First Total Synthesis of a Polyunsaturated Chromone Metabolite Isolated from the Brown Algae *Zonaria tournefortii*", *Org. Letters*, 11(3), 587-588 (2009).

This invention will be further clarified by a consideration of the following examples for synthesis of compounds of Formula (I), which are intended to be purely exemplary of the present invention. The examples for EPA-TZ and DHA-TZ are generally applicable to all PUFAs.

Example 1

Synthesis of 5-((5Z,8Z,11Z,14Z,17Z)-eicosa-5,8,11,14,17-pentaenyl)thiazolidine-2,4-dione, (EPA-TZ conjugate)

This EPA-TZ conjugate preparation is outlined in Scheme 1 below.

Scheme 1

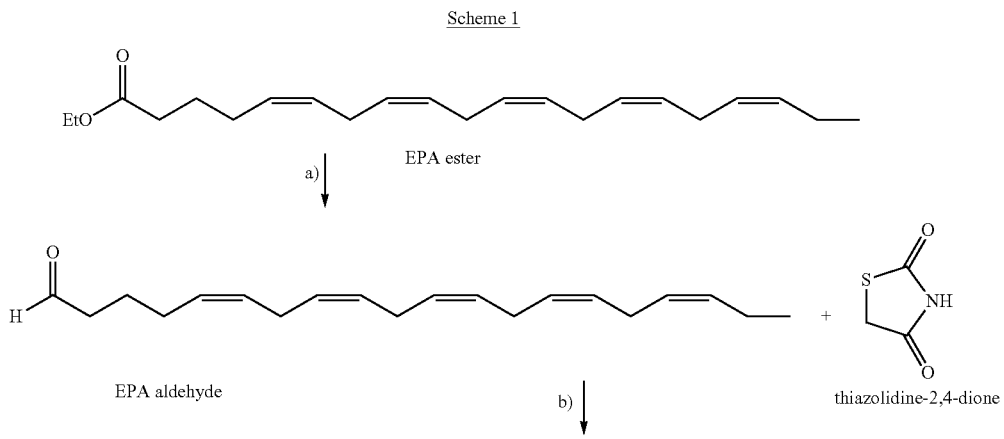

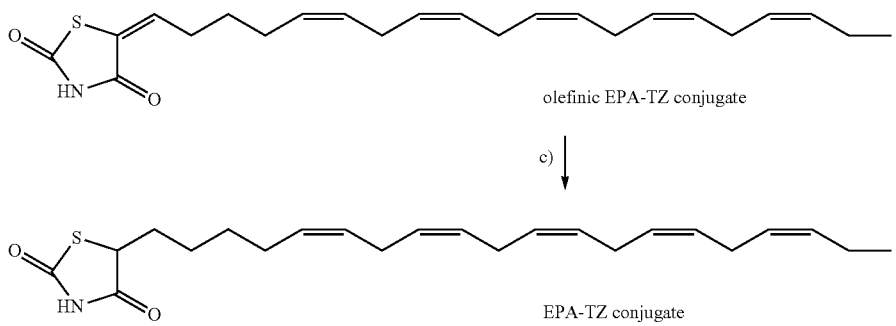

olefinic EPA-TZ conjugate c)

EPA-TZ conjugate a) DIBAH, CH$_2$Cl$_2$, -78° C.; b) piperidine, ethanol, reflux, 3 h; c) NaBH$_4$, CoCl$_2$, dimethylglyoxime, methanol, DMF, water, 30-40° C., 5 h.

Procedure:

EPA ethyl ester (65%, TCI America, 25.0 g, 0.076 mol) was dissolved in dichloromethane (120 mL) under an argon atmosphere. The solution was cooled in acetone/dry ice batch and 1M diisobutylaluminum hydride (140 mL) in dichloromethane was added dropwise over 1 h, while cooling in an acetone/dry ice bath. After the addition was complete, the solution was stirred for 3 h at −78° C. The reaction mixture was quenched with saturated ammonium chloride (100 mL) added dropwise, followed by 5% aqueous HCl (100 mL). Additional dichloromethane (200 mL) was added and the mixture warmed to RT. After filtration, the dichloromethane layer was separated, dried over sodium sulfate, filtered, and concentrated. The crude EPA aldehyde (15.8 g yellow oil) was purified by column chromatography on silica gel (300 g) eluting with ethyl acetate/heptanes (1:10) to yield EPA aldehyde (8.85 g, 40% yield, 65-70% purity by NMR) as a clear oil.

The EPA aldehyde (8.85 g, 0.031 mol) and 2,4-thiazolidinedione (4.6 g, 0.039 mol) were dissolved in ethanol (150 mL) under an argon atmosphere at RT. Piperidine (0.60 mL, 0.006 mol) was added and the solution was heated under reflux for 3 h. The solution was cooled to RT and concentrated under reduced pressure. Dichloromethane (100 mL) was added. The dichloromethane solution was washed with 5% aqueous hydrochloric acid (100 mL) and water (100 mL). The solution was then dried over sodium sulfate, filtered, and concentrated under reduced pressure. The crude condensed EPA-TZ conjugate was purified by column chromatography on silica gel (250 g) eluting with ethyl acetate/heptanes (1:3) to produce the olefinic EPA-TZ conjugate (8.65 g, 73% yield) as a yellow oil (purity 65-70% by NMR).

In a separate flask, dimethylglyoxime (6.6 g, 0.057 mol) and cobalt chloride hexahydrate (1.3 g, 0.0054 mol) were mixed in DMF (60 mL). The olefin was dissolved in methanol (100 mL) and sodium hydroxide (1.3 g, 0.033 mol) in water (60 mL) was added. After mixing, the cobalt chloride/dimethylglyoxime solution was added to the olefin. The mixture was warmed to 30-40° C. on a water bath and sodium borohydride (2.0 g) was added in portions over 3 h. After a total of 5 h at 30-40° C., the mixture was cooled to RT and concentrated under reduced pressure. The crude material was added to dichloromethane (200 mL) and washed with 5% hydrochloric acid (200 mL). The dichloromethane solution was dried over sodium sulfate, filtered, and concentrated. The crude orange oil (9.5 g) was purified by column chromatography on silica gel (200 g) eluting with ethyl acetate/heptanes (1:4). The procedure generated the EPA-TZ conjugate (6.2 g, 72% yield, 70% purity by HPLC) as a light yellow oil. The EPA-TZ conjugate was purified in portions (0.8 g) twice, by reverse phase chromatography on a C18 cartridge (100 g) using an automated MPLC system (Combi-flash), eluting with 40-90% methanol/water over 24 min and 90% methanol/water over 20 min (observing at 233 nm, rt=32-34 min) The MPLC purification, after concentration and drying, generated 0.63 g light tan gel that was EPA-TZ conjugate (95.8% purity, HPLC) and is further characterized by:

Appearance: colorless oil

Chemical Formula: $C_{23}H_{33}NO_2S$; Molecular Weight: 387.58

Chromatographic purity (HPLC): 95.8% (rt=11.735 min, 80-95% MeOH/H$_2$O over 10 min, Luna C18, 5μ, 4.6×250 mm, 1.0 mL/min, 10 μL injection, 40° C., UV detection, 230 nm)

HRMS (MMI-TOF-MS): Calculated for $C_{23}H_{34}NO_2S$ $(M+H)^+$: 388.2310. found: 388.2314.

$^1$H NMR (300 MHz, CDCl$_3$/TMS): δ 8.51 (s, 1H), 5.42-5.27 (m, 10H), 4.27 (dd, 1H, J=9.3, 4.2 Hz), 2.90-2.75 (m, 8H), 2.21-2.00 (m, 5H), 1.99-1.96 (m, 1H), 1.58-1.38 (m, 4H), 0.98 (t, 3H J=7.8 Hz)

$^{13}$C NMR (75 MHz, CDCl$_3$/TMS): δ 175.7, 171.4, 132.1, 129.4, 128.6, 128.4, 128.3, 128.2, 128.1, 127.9, 127.1, 52.0, 32.9, 29.1, 27.0, 26.8, 25.9, 25.8, 20.8, 14.5.

Example 2

Synthesis of 5-((4Z,7Z,10Z,13Z,16Z,19Z)-docosa-4,7,10,13,16,19-hexaenyl)thiazolidine-2,4-dione (DHA-TZ)

Synthesis of 5-((4Z,7Z,10Z,13Z,16Z,19Z)-docosa-4,7,10,13,16,19-hexaenyl)thiazolidine-2,4-dione (DHA-TZ) is outlined in Scheme 2 below.

Scheme 2

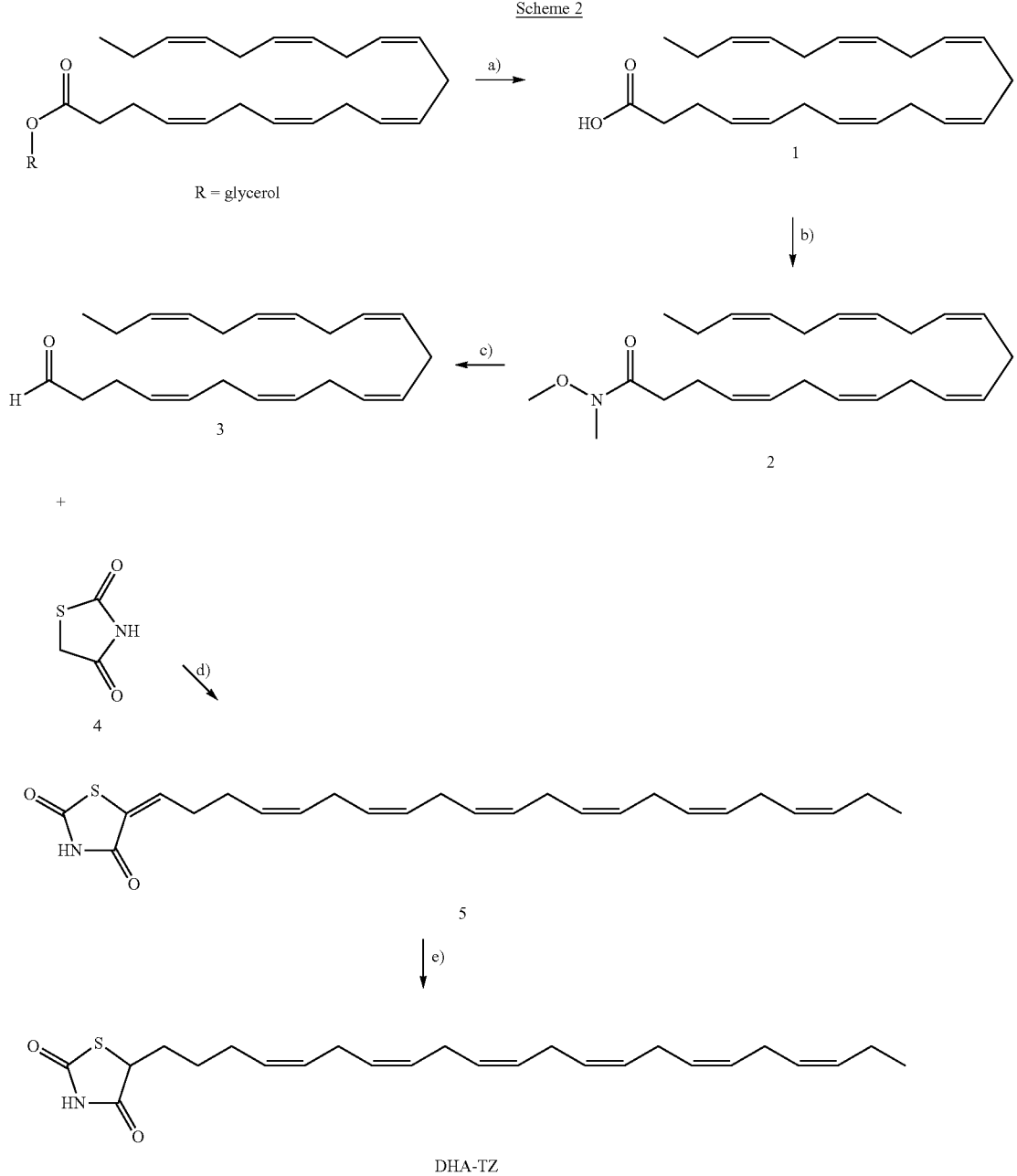

a) NaOH, water, methanol, THF, RT overnight; b) CH$_3$NHOCH$_3$, EDC, DMAP, CH$_2$Cl$_2$, RT 20 h; c) LAH, Et$_2$O, -40 to 5° C., 2 h; d) piperidine, ethanol, reflux, 3 h; e) NaBH$_4$, CoCl$_2$, dimethylglyoxime, methanol, DMF, water, 30-40° C., 5 h.

Procedure:
Part A: Starting Material, DHA as the Free Acid

DHA-Aid CL-400 (40%, Lonza, 20.0 g) which contained bis and triglycerides of DHA and other fatty acids, was mixed with THF (200 mL), methanol (200 mL), and water (200 mL) containing sodium hydroxide (40 g, 1 mol) at RT overnight under an argon atmosphere. After 20 h, the solution was concentrated by 50% on a rotary evaporator. The solids that formed were washed with THF (50 mL). The THF filtrates were combined and concentrated. Water (100 mL) was added and the mixture was acidified to pH 2 with concentrated HCl. The product was extracted with diethyl ether (2×100 mL). The ether extracts were combined, dried over sodium sulfate, filtered, and concentrated. The remaining yellow solid (6.5 g) was dissolved in heptanes (200 mL) and stored overnight in a −10° C. freezer. The solids were filtered and the DHA enriched filtrate was concentrated. The process generated a mixture of acids that was roughly 50-60% DHA acid (1 in Scheme 2), as a yellow oil, and is further characterized by:

¹H NMR (300 MHz, CDCl₃/TMS): major component δ 5.42-5.27 (m, 12H), 2.90-2.75 (m, 10H), 2.40-2.25 (m, 4H), 2.21-2.00 (m, 2H), 0.98 (t, 3H J=7.8 Hz).

Part B: (4Z,7Z,10Z,13Z,16Z,19Z)—N-methoxy-N-methyl-docosa-4,7,10,13,16,19-hexaenamide

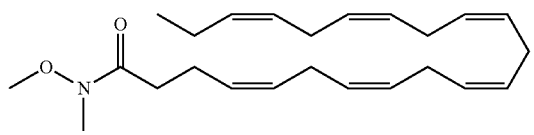 [SMILES: CC/C=C\C/C=C\C/C=C\C/C=C\C/C=C\C/C=C\CCC(=O)N(C)OC]

The DHA acid mixture 1 (4.68 g, 14.2 mmol) was dissolved in dichloromethane (20 mL) under an argon atmosphere, at RT. To the DHA solution, was added N,O-dimethylhydroxylamine hydrochloride (1.39 g, 14.2 mmol), 4-(N,N-dimethylamino)pyridine (1.74 g, 14.2 mmol), and EDC (3.0 g, 15.6 mmol). After stiffing for 20 h at RT, the solution was extracted with 10% hydrochloric acid solution (2×150 mL). The dichloromethane was dried over sodium sulfate, filtered, and concentrated. The crude product (5.0 g tan oil) was purified on silica gel (100 g) eluting with ethyl acetate/heptanes (1:20) to generate the DHA-amide mixture (2 in Scheme 2) (4.7 g, 89% yield) as a tan oil that was 60-65% DHA-amide by NMR and is further characterized by:

¹H NMR (300 MHz, CDCl₃/TMS): major component δ 5.45-5.26 (m, 12H), 3.64 (s, 3H), 3.14 (s, 3H), 2.90-2.75 (m, 10H), 2.50-2.35 (m, 4H), 2.04 (m, 2H), 0.97 (t, 3H J=7.5 Hz);

¹³C NMR (75 MHz, CDCl₃/TMS): major component δ 173.8, 131.9, 128.8, 128.6, 128.5, 128.2, 128.1, 128.0, 127.8, 127.0, 32.0, 25.8, 25.7, 22.6, 20.7, 14.4.

Part C: (4Z,7Z,10Z,13Z,16Z,19Z)-docosa-4,7,10,13,16,19-hexaenal

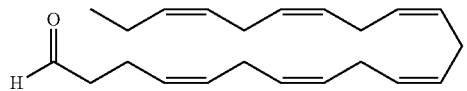 [SMILES: CC/C=C\C/C=C\C/C=C\C/C=C\C/C=C\C/C=C\CCC=O]

DHA amide from Part B (3.55 g, 9.55 mmol) was dissolved in diethyl ether (15 mL) under an argon atmosphere. The DHA solution was added drop-wire to a mixture of lithium aluminum hydride (0.55 g, 14.5 mmol) in diethyl ether (50 mL) that was cooled in acetone/dry ice batch that maintained the temperature at or below −50° C. After the addition was complete, the solution was stirred and slowly warmed for 3 h to 0° C. The flask was cooled again to −50° C. and the experiment was quenched by drop-wise addition of potassium bisulfate (1.6 g) in water (15 mL). Additional diethyl ether (50 mL) was added and the mixture warmed to 0° C. After filtration, the salts were washed with additional diethyl ether (2×50 mL). The combined diethyl ether extracts were dried over sodium sulfate, filtered, and concentrated. The crude DHA aldehyde (2.9 g colorless oil) was purified twice by column chromatography on silica gel (100 g) eluting with ethyl acetate/heptanes (1:20) to prepare DHA aldehyde (3 in Scheme 2) (0.7 g, 23% yield, 85-90% purity by NMR) as a clear oil and further characterized by:

¹H NMR (300 MHz, CDCl₃/TMS): δ 9.78 (s, 1H), 5.50-5.22 (m, 12H), 2.90-2.75 (m, 10H), 2.51-2.45 (m, 4H), 2.08 (m, 2H), 0.98 (t, 3H J=7.5 Hz);

¹³C NMR (75 MHz, CDCl₃/TMS): δ 201.7, 132.2, 128.6, 128.7, 128.6, 128.5, 128.1, 127.9, 127.2, 44.0, 26.0, 25.9, 20.9, 20.5, 14.6.

Part D: (E)-5-((4Z,7Z,10Z,13Z,16Z,19Z)-docosa-4,7,10,13,16,19-hexaenylidene)thiazolidine-2,4-dione

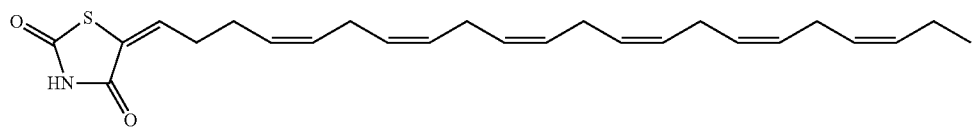 [SMILES: CC/C=C\C/C=C\C/C=C\C/C=C\C/C=C\C/C=C\CC/C=C1/SC(=O)NC1=O]

DHA aldehyde from Part C (1.50 g, 4.8 mmol) was dissolved in ethanol (30 mL) with thiazolidine-2,4-dione (0.81 g, 6.8 mmol), and a catalytic amount of piperidine (103 mg, 1.2 mmol). The mixture was heated under reflux for 2 h. The heat was turned off and the solution slowly cooled to RT over 1.5 h. The ethanol was removed under reduced pressure and dichloromethane (100 mL) was added. The dichloromethane was extracted with 5% HCl (100 mL) and water (100 mL). The dichloromethane was dried over sodium sulfate, filtered, and concentrated. The remaining orange oil (1.94 g) was purified on silica gel (100 g), eluting with 10-30% ethyl acetate in heptanes. The experiment produced DHA-TZ olefin intermediate (4 in Scheme 2) (1.45 g, 74% yield, purity 85-90% by NMR) as a light yellow oil and is further characterized by:

¹H NMR (300 MHz, CDCl₃/TMS): δ 7.04 (t, 1H, J=7.5 Hz), 5.50-5.22 (m, 12H), 2.85-2.75 (m, 10H), 2.40-2.25 (m, 4H), 2.08 (m, 2H), 0.98 (t, 3H J=7.5 Hz);

¹³C NMR (75 MHz, CDCl₃/TMS): δ 167.0, 165.2, 138.6, 132.2, 130.2, 128.7, 128.6, 128.5, 128.5, 128.2, 128.1, 128.0, 127.8, 127.5, 127.1, 126.9, 32.1, 26.0, 25.9, 25.8, 20.9, 14.6.

Part E: 5-((4Z,7Z,10Z,13Z,16Z,19Z)-docosa-4,7,10,13,16,19-hexaenyl)thiazolidine-2,4-dione, a compound of Formula (I)

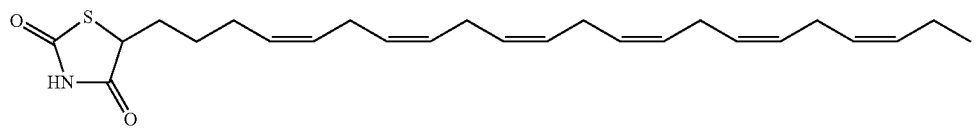 [SMILES: CC/C=C\C/C=C\C/C=C\C/C=C\C/C=C\C/C=C\CCCC1SC(=O)NC1=O]

DHA-TZ olefin intermediate from Part D (0.62 g, 1.5 mmol) was mixed with methanol (12 mL) and sodium hydroxide (0.2 g, 5 mmol) in water (5 mL) at RT for 5 min To this solution was added a mixture of dimethlglyoxime (0.54 g, 4.6 mmol) and cobalt chloride hexahydrate (0.2 g, 0.84 mmol) in DMF (10 mL). The solution was heated to 30-40° C. and sodium borohydride (450 mg, 10.5 mmol) was added in portions over 5 h. After 5 h, the solution was cooled to RT in a water bath and diluted hydrochloric acid was added (100 mL, 5% HCl). The product was extracted twice with diethyl ether (100 mL each). The combined diethyl ether extracts were dried over sodium sulfate, filtered, and concentrated. The crude product was purified on silica gel (10 g) eluting with 0-30% ethyl acetate in heptane to made DHA-TZ analog (5 in Scheme 2) (0.22 g, 35% yield) as clear oil and is further characterized by:

Appearance: colorless oil;
Chemical Formula: $C_{25}H_{35}NO_2S$; Molecular Weight: 413.62;
HRMS (MMI-TOF-MS): Calculated for $C_{25}H_{36}NO_2S$ $(M+H)^+$: 414.2466. found: 414.2477.
$^1H$ NMR (300 MHz, $CDCl_3$/TMS): δ 8.26 (br s, 1H), 5.50-5.27 (m, 12H), 4.27 (dd, 1H, J=9.3, 4.2 Hz), 2.90-2.75 (m, 10H), 2.21-1.95 (m, 5H), 1.66-1.42 (m, 2H), 0.97 (t, 3H J=7.5 Hz);
$^{13}C$ NMR (75 MHz, $CDCl_3$/TMS): δ 174.4, 170.1, 132.2, 129.3, 128.8, 128.5, 128.3, 128.2, 128.1, 127.2, 51.9, 32.8, 27.1, 26.8, 26.0, 25.9, 20.9, 14.6; and
HPLC Purity: 90%.

In Vitro Biology:

The proposed anti-diabetic mechanism of action of the compounds of Formula (I) includes the activation of PPARγ, which is well known to induce metabolic changes that ameliorate diabetes. To determine if these compounds can activate PPARγ or the members of the PPAR family of nuclear receptors (PPARα and PPARδ), the ability of these compounds to activate PPAR receptors in a cell-based chimeric receptor transcription assay were tested. This is a standard nuclear receptor ligand activity assay that utilizes the ligand binding domain of the PPAR receptor fused to a heterologous GAL4 DNA binding domain. The transcriptional read-out is from a GAL4-regulated luciferase reporter. In this assay, compounds that activate the receptor cause an increase in luciferase activity measured in a luminometer. The data are shown in Table 1 below (average luciferase values from transcription assay).

TABLE 1

| µM conc. | Compound Tested | Rosiglitazone PPARγ | EPA Et Ester | EPA-TZ | DHA-TZ |
|---|---|---|---|---|---|
| 40 | | | 261* | 48^ | 1868* |
| 20 | | 5575* | | | |
| 16 | | | 224* | 1416* | 1454* |
| 8 | | 4621* | | | |
| 6.4 | | | 122 | 705* | 623* |
| 3.2 | | 3941* | | | |
| 2.6 | | | 120 | 297* | 207* |
| 1.3 | | 3729* | | | |
| 1.02 | | | 89 | 164* | 167* |
| 0.51 | | 3828* | | | |
| 0.41 | | | 105 | 123 | 145 |
| 0.20 | | 3459* | | | |
| 0.16 | | | 108 | 128 | 106 |
| 0.08 | | 2301* | | | |
| 0.03 | | 1205* | | | |
| 0.01 | | 482* | | | |

^reduced cell viability;
*above background

Even though it was not possible to calculate an $EC_{50}$ value for the EPA ethyl ester as control, it is notable that it showed a mild stimulatory activity on PPARγ at high doses (Table 1).

Given that the goal of the present medicinal chemistry strategy was to increase the PPARγ stimulatory activity of EPA, these data clearly show that the strategy was a success. The results of this assay demonstrate the EPA-TZ and DHA-TZ induced the activation of PPARγ with a potency ($EC_{50}$) of 12 and 10 µmolar, respectively.

Table 2 below is a summary of the calculated $EC_{50}$ values and a graph of the dose response curves are shown in FIG. 1.

TABLE 2

| Compound | EC50 µM | RE | RE Conc. µM |
|---|---|---|---|
| Rosiglitazone PPARγ | 0.11 | 5475 | 20 |
| EPA Et Ester | >100 | 300 | 100 |
| EPA-TZ | 12 | 1316 | 16 |
| DHA-TZ | 9.7 | 1354 | 16 |

These measurements of agonist activity show a 10 fold increase in activity.

The ability of EPA-TZ and DHA-TZ to activate PPARγ is similar to troglitazone and pioglitazone (PPARγ ligands used as antidiabetic agents in humans), both of which have potency in the same low micro molar range (see T Wilson, et al., "The PPARs: from Orphan Receptors to Drug Discovery", *J. Med. Chem.* 43(4), 527-50 (2000 Feb. 24)).

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. Accordingly, this description is to be construed as illustrative only and is for the purpose of teaching those skilled in the art the general manner of carrying out the invention.

What is claimed is:
1. Compounds of Formula (I)

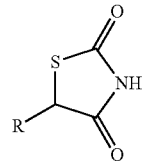

Formula (I)

wherein:
R is joined from the methylene moiety formed by reduction of the carboxylic acid of one of the following acids:
cis,cis,cis-7,10,13-hexadecatrienoic acid (HTA), named as RS-5-((7Z,10Z,13Z)-hexadeca-7,10,13-trien-1-yl)thiazolidine-2,4-dione;
cis,cis,cis-9,12,15-octadecatrienoic acid (ALA), named as RS-5-(9Z,12Z,15Z)-octadeca-6,9,12-trien-1-yl)thiazolidine-2,4-dione;
cis,cis,cis,cis-6,9,12,15-octadecatetraenoic acid (SDA), named as RS-5-((6Z,9Z,12Z,15)-octadeca-6,9,12,15-tetraen-1-yl)thiazolidine-2,4-dione;
cis,cis,cis-11,14,17-eicosatrienoic acid (ETE), named as RS-5-((11Z,14Z,17Z)-eicosa-11,14,17-triene-1-yl) thiazolidine-2,4-dione;
cis,cis,cis,cis-8,11,14,17-eicosatetraenoic acid (ETA), named as RS-5-((8Z,11Z,14Z,17Z)-eicosa-8,11,14,17-tetraen-1-vi)thiazoliidine-2,4-dione;

cis,cis,cis,cis,cis-5,8,11,14,17-eicosapentanenoic acid (EPA), named as RS-5-((5Z,8Z,11Z,14Z,17Z)-eicosa-5,8,11,14,17-pentaen-1-yl)thiazolidine-2,4-dione;

cis,cis,cis,cis,cis-6,9,12,15,18-heneicosapentaenoic acid (HPA), named as RS-5-((6Z,9Z,12Z,15Z,18Z)-heneicosa-6,9,12,15,18-pentaen-1-yl)thiazolidine-2,4-dione:

cis,cis,cis,cis,cis-7,10,13,16,19-docosapentaenoic acid (DPA), named as RS-5-((7Z,10Z,13Z,16Z,19Z)docosa-7,10,13,16,19-pentaen-1-yl)thiazolidine-2,4-dione;

cis,cis,cis,cis,cis,cis-4,7,10,13,16,19-docosahexaenoic acid (DHA), named as RS-5-((4Z,7Z,10Z,13Z,16Z,19Z)docosa-4,7,10,13,16,19-hexaen-1-yl)thiazolidine-2,4-dione;

cis,cis,cis,cis,cis-9,12,15,18,21-tetracosapentaeonic acid (TPA), named as RS-5-((9Z,12Z,15Z,18Z,21Z)-tetracosa-9,12,15,18,21-pentaen-1-yl)thiazolidine-2,4-dione; or cis,cis,cis,cis,cis,cis-6,9,12,15,18,21-tetracosahexaeonic acid (THA), named as RS-5-((6Z,9Z,12Z,15Z,18Z,21Z)-tetracosa-6,9,12,15,18,21-hexaen-1-yl)thiazolidine-2,4-dione.

2. The compound of claim 1 wherein the compound has a chemical purity of ≥90%.

3. A pharmaceutical formulation comprising as its active ingredient one or more compounds of Formula (I) as defined in claim 1 or its pharmaceutically-acceptable salts, together with one or more pharmaceutically-acceptable adjuvants, binders, desiccants, diluents and excipients.

4. The pharmaceutical formulation of claim 3 in the form of a solution for injection, gelatin capsule or tablet.

5. The pharmaceutical formulation of claim 3 for the treatment of Type2 diabetes, wherein the formulation includes metformin hydrochloride, as a single formulation.

6. The pharmaceutical formulation of claim 3 for the treatment of or slowing down the progression of Alzheimer's disease, wherein the compound of Formula (I) is RS-5-((4Z,7Z,10Z,13Z,16Z,19Z)docosa-4,7,10,13,16,19-hexaen-1-yl)thiazolidine-2,4-dione: that is derived from cis,cis,cis,cis,cis,cis-4,7,10,13,16,19-docosahexaenoic acid (DHA).

7. A method for the treatment of Type2 diabetes and/or hypertriglycerdemia which comprises administration of a solution for injection, gelatin capsule or tablet of an effective amount of a formulation of claim to a human in need of such treatment.

8. The method of claim 7 wherein the effective amount is a dose from about 0.05 to about 5 g/day, at 1-4 closes/day.

9. The method of claim 7 for the treatment of Type2 diabetes wherein the formulation is concurrently administered with metformin hydrochloride, at about 500 mg as a dose, at 2 doses/day.

10. The method of claim 7 wherein the formulation includes metformin hydrochloride, at a dose of about 500 mg, at 2 doses/day, as a single formulation or concurrently administered combination.

11. A method for the treatment of or in slowing down the progression of the early stages of Alzheimer's disease, which comprises administration of a solution for injection, gelatin capsule or tablet of an effective amount of a formulation of claim 6 to a human in need of such treatment.

12. The method of claim 11, wherein the effective amount is a dose from about 0.05 to about 5 g/day, at 1-4 doses/day.

13. The pharmaceutical formulation of claim 4 for the treatment of Type2 diabetes, wherein the formulation includes metformin hydrochloride, as a single formulation.

14. The pharmaceutical formulation of claim 4 for the treatment of or slowing down the progression of Alzheimer's disease, wherein the compound of Formula (I) is RS-5-((4Z,7Z,10Z,13Z,16Z,19Z)docosa-4,7,10,13,16,19-hexaen-1-yl)thiazolidine-2,4-dione; that is derived from cis,cis,cis,cis,cis,cis-4,7,10,13,16,19-docosahexaenoic acid (DHA).

15. The method of claim 7 for the treatment of Type2 diabetes wherein the formulation is in the form of a solution for injection, gelatin capsule or tablet and is concurrently administered with metformin hydrochloride, at about 500 mg as a dose, at 2 doses/day.

16. The method of claim 7 wherein the formulation is in the form of a solution for injection, gelatin capsule or tablet and includes metformin hydrochloride, at a dose of about 500 mg, at 2 doses/day, as a single formulation or concurrently administered combination.

* * * * *